(12) United States Patent
Chuang et al.

(10) Patent No.: US 9,127,323 B2
(45) Date of Patent: Sep. 8, 2015

(54) ISOLATED YEAST STRAIN HAVING HIGH XYLOSE CONSUMPTION RATE AND PROCESS FOR PRODUCTION OF ETHANOL USING THE STRAIN

(71) Applicants: Yu-Chuan Chuang, Taipei (TW); Shiou-Hung Tsai, Taipei (TW)

(72) Inventors: Yu-Chuan Chuang, Taipei (TW); Shiou-Hung Tsai, Taipei (TW)

(73) Assignee: Far Eastern New Century Corporation, Taipei (TW)

( * ) Notice: Subject to any disclaimer, the term of this patent is extended or adjusted under 35 U.S.C. 154(b) by 307 days.

(21) Appl. No.: 13/628,910

(22) Filed: Sep. 27, 2012

(65) Prior Publication Data

US 2014/0087438 A1    Mar. 27, 2014

(51) Int. Cl.
 *C12N 1/15*    (2006.01)
 *C12P 7/10*    (2006.01)
 *C12R 1/865*   (2006.01)
 *C12N 9/04*    (2006.01)
 *C12N 9/12*    (2006.01)
 *C12N 9/92*    (2006.01)
 *C12N 1/18*    (2006.01)

(52) U.S. Cl.
 CPC . *C12R 1/865* (2013.01); *C12N 1/18* (2013.01); *C12N 9/0006* (2013.01); *C12N 9/1205* (2013.01); *C12N 9/92* (2013.01); *C12P 7/10* (2013.01); *C12Y 101/01307* (2013.01); *C12Y 207/01017* (2013.01); *C12Y 503/01005* (2013.01); *Y02E 50/16* (2013.01); *Y02E 50/17* (2013.01)

(58) Field of Classification Search
 CPC .......... C12N 1/18; C12N 9/0006; C12P 7/10; C12Y 101/01307
 USPC ............................................ 435/254.21, 161
 See application file for complete search history.

(56) References Cited

FOREIGN PATENT DOCUMENTS

CA    2176038 C    8/2006
FI    104636 B    3/2000

OTHER PUBLICATIONS

Translation of Search Report dated Apr. 15, 2014 for corresponding Taiwan Patent Application No. 101135655.
Jeffries, T.W., et al., *Metabolic engineering for improved fermentation of pentoses by yeasts* (2004), Appl. Microbiol. Biotechnol., 63(5): pp. 495-509.
Krishnan, M.S., et al., *Fermentation kinetics of ethanol production from glucose and xylose by recombinant Saccharomyces 1400 (pLNH33)* (Spring 1999), Appl. Biochem. Biotechnol., vol. 78, Issue 1-3, pp. 373-388.
Casey, Elizabeth et al., "Effect of acetic acid and pH on the cofermentation of glucose and xylose to ethanol by a genetically engineered strain of *Saccharomyces cerevisiae*," FEMS Yeast Res., vol. 10, 2010, pp. 385-393.
Johansson, Björn et al., "The non-oxidative pentose phosphate pathway controls the fermentation rate of xylose but not of xylose in *Saccharomyces cerevisiae* TMB3001," FEMS Yeast Res., vol. 2, 2002, pp. 227-282.
"Search Report dated Nov. 24, 2014," Chinese Application No. 201310074168.2, 5 pages.

*Primary Examiner* — Tekchand Saidha
*Assistant Examiner* — MD. Younus Meah
(74) *Attorney, Agent, or Firm* — Novak Druce Connolly Bove + Quigg LLP

(57) ABSTRACT

The invention utilizes cloning and transformation techniques in combination with mutation and strain taming techniques to obtain yeasts having high xylose consumption rate and ethanol yield. The cloning and transformation used in the invention are to transform xylose metabolism genes to yeasts to solve the problem that some yeast strains cannot utilize xylose to produce ethanol. The mutation and strain taming used in the invention are to increase xylose consumption rate and ethanol yield to solve the problem of low rate and yield. By combining the above-mentioned technical means, the invention unexpectedly obtain a mutant having high xylose consumption rate and ethanol yield.

4 Claims, 2 Drawing Sheets

US 9,127,323 B2

ISOLATED YEAST STRAIN HAVING HIGH XYLOSE CONSUMPTION RATE AND PROCESS FOR PRODUCTION OF ETHANOL USING THE STRAIN

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_22171_00151. The size of the text file is 2.10 KB, and the text file was created on Sep. 27, 2012.

FIELD OF THE INVENTION

The present invention relates to an isolated yeast strain having high xylose consumption rate and a fermentation process for production of ethanol. In particular, the present invention provides *Saccharomyces* strains with high xylose consumption rate.

BACKGROUND OF THE INVENTION

Large-scale consumption of the traditional, fossil fuels (petroleum-based fuels) in the last few decades has contributed to high cost and high levels of pollution. Moreover, the realization that the world stock of petroleum is not boundless, combined with the growing environmental awareness, has stimulated new initiatives to investigate the feasibility of alternative fuels such as cellulosic ethanol, which can reduce $CO_2$ production.

Processes presently employed for the production of ethanol include the following operational phases: (a) fermentation of the appropriate raw materials to obtain fermented products and (b) distillation of the products obtained by fermentation whereby ethanol is produced. A yeast belonging to the genus *Saccharomyces*, *Saccharomyces cerevisiae*, has been mainly used as a seed strain for ethanol fermentation. *Saccharomyces cerevisiae* cells are round to ovoid, 5-10 micrometers in diameter and can efficiently utilizes hexose including glucose, mannose, galactose etc. The fermentation process mentioned above includes seeding *Saccharomyces cerevisiae* is a medium containing nitrogen source, carbon source and trace elements etc. and performing fermentation under appropriate conditions, and it involve the chemical reaction: $C_6H_{12}O_6 \rightarrow 2\ CH_3CH_2OH + 2\ CO_2$.

Various sources of biomass can be used for alcohol production. The many and varied raw materials used in the manufacture of ethanol via fermentation are conveniently classified under three types of agricultural raw materials: sugar, starches, and lignocellulose materials. Although biomass-derived ethanol may be produced by fermentation of sugars or starches that are obtained from many different sources, so far, however, the substrates for industrial scale production or fuel alcohol are cane sugar and corn starch. The techniques of using sugars or starches to produce ethanol are well-developed; however, these substrates are of the high costs, it may take away from food supply and the production of ethanol from these sources is insufficient in meeting future demands for fuel industry. Therefore, there is a growing interest in producing ethanol from lignocelluloses. Lignocelluloses is a desirable alternative over other ethanol feedstocks such as corn grain since it is renewable, abundant, does not take away from the food supply and is available at a relatively low cost. Expanding fuel ethanol production requires the ability to use lower-cost feedstocks. Presently, only lignocellulosic feedstock from plant biomass would be available in sufficient quantities to substitute the crops used for ethanol production. The major fermentable sugars from lignocellulosic materials are glucose and xylose, constituting respectively about 40% and 25% of lignocellulose.

However, most yeasts that are capable of alcoholic fermentation, like *Saccharomyces cerevisiae*, are not capable of using xylose as a carbon source. To enable the commercial production of ethanol from lignocellulose hydrolysate, an organism possessing both these properties would be required. Scientists utilize genetic technology or strain taming to improve fermentation of xylose by yeasts or bacteria for the production of ethanol. U.S. Pat. No. 5,789,210 provides yeast strains capable of effectively fermenting xylose alone or simultaneously with glucose can be created using recombinant DNA and gene cloning techniques and these techniques have been used to create recombinant yeasts containing cloned xylose reductase (XR), xylitol dehydrogenase (XD), and xylulokinase (XK) genes which are fused to promotors not inhibited by the presence of glucose. U.S. Pat. No. 6,582,944 relates to new recombinant yeast strains transformed with xylose reductase and/or xylitol dehydrogenase enzyme genes, which is capable of reducing xylose to xylitol and consequently of producing xylitol in vivo. Bjorn et al. provide a yeast strain, TMB 3001, by transforming it with xylase reductase and/or xylitol dehydrogenase enzyme genes to solve the problem of being unable to metabolism xylose to produce ethanol (Biorn J, Barbel H H. The non-oxidative pentose phosphate pathway controls the fermentation rate of xylose but not of xylose in TMB 3001, 2002, *FEMS Yeast Research* 2:227-282). However, it still has the following problems: low xylose consumption rate (0.13 g xylose/g biomass/hour) and low ethanol yield (0.15 g product/g consumed xylose). To solve these problems, Johansson et al. further transform transaldolase gene to *Saccharomyces cerevisiae* to obtain a new strain, TMB 3026, which can increase xylose consumption rate from 0.12 to 0.23. (Biorn J, Barbel H H. The non-oxidative pentose phosphate pathway controls the fermentation rate of xylose but not of xylose in TMB 3001, 2002, *FEMS Yeast Research* 2:227-282); however, the requirements for industrial production still have not been met. Kaisa et al. further create a transformed yeast, TMB 3057, having an improved gene expression in xylose reductase and/or xylitol dehydrogenase and a deleted aldose reductase gene (GR3) to elevate ethanol yield and reduce formation of xylitol by-product (Kaisa K, Romain F, Barbel H H, Marie G G High activity of xylose reductase and xylitol dehydrogenase improves xylose fermentation by recombinant *Saccharomyces cerevisiae*, 2007, Appl. Microbiol. Biotechnol. 73: 1039-1046). However, this strain still has the problems of low xylose consumption rate (0.25 g xylose/g biomass/hour and low ethanol yield (0.27 g product/g consumed xylose). Furthermore, Elizebath et al. use gene modified yeast 422A (LNH-ST) that is transformed with xylose reductase gene of N crasser and *C. parapsilosis* and xylitol dehydrogenase gene of *P. stipitis* and has optimized codons of three amino acids (Eliabeth C, Miroslav S., Nancy W Y H, Nathan S M, Effect of acetic acid and pH on the cofermentation of glucose and xylose to ethanol by a genetically engineered strain of *Saccharomyces cerevisiae*, 2010, FEMS Yeast Res. 10:385-393). This stain also utilizes GAPDH promoter to control pentose phosphate pathway of TKL1, TAL1, RKL1 and RPE1. However, it still has the following problems: low xylose consumption rate (0.27 g xylose/g biomass/hour at pH5) and low ethanol yield (0.785 g product/g consumed xylose) and low tolerance to acetic acid (the xylose consumption rate reduces to 015 from 0.354 when the medium contains 1 g/L acetic acid).

Therefore, there is a significant need in the art for a strain that provide for improved biomass (such as xylose) conversion to ethanol and a method for production of ethanol in higher yield.

SUMMARY OF THE INVENTION

The invention provides an isolated yeast strain which has xylose consumption rate higher than 1.1 g xylose/gram biomass/hour and comprises one or more xylose metabolism gene obtained from strain *Saccharomyces cerevisiae* FENC-000 with DSMZ Deposit No, 25508.

The invention further provides a process for producing ethanol, comprising the steps of: (a) fermenting medium containing a source of xylose or glucose with an isolated yeast strain according to the invention under a suitable fermentation condition; and (b) recovering the ethanol from said medium.

DETAILED DESCRIPTION OF THE INVENTION

Figure 1:
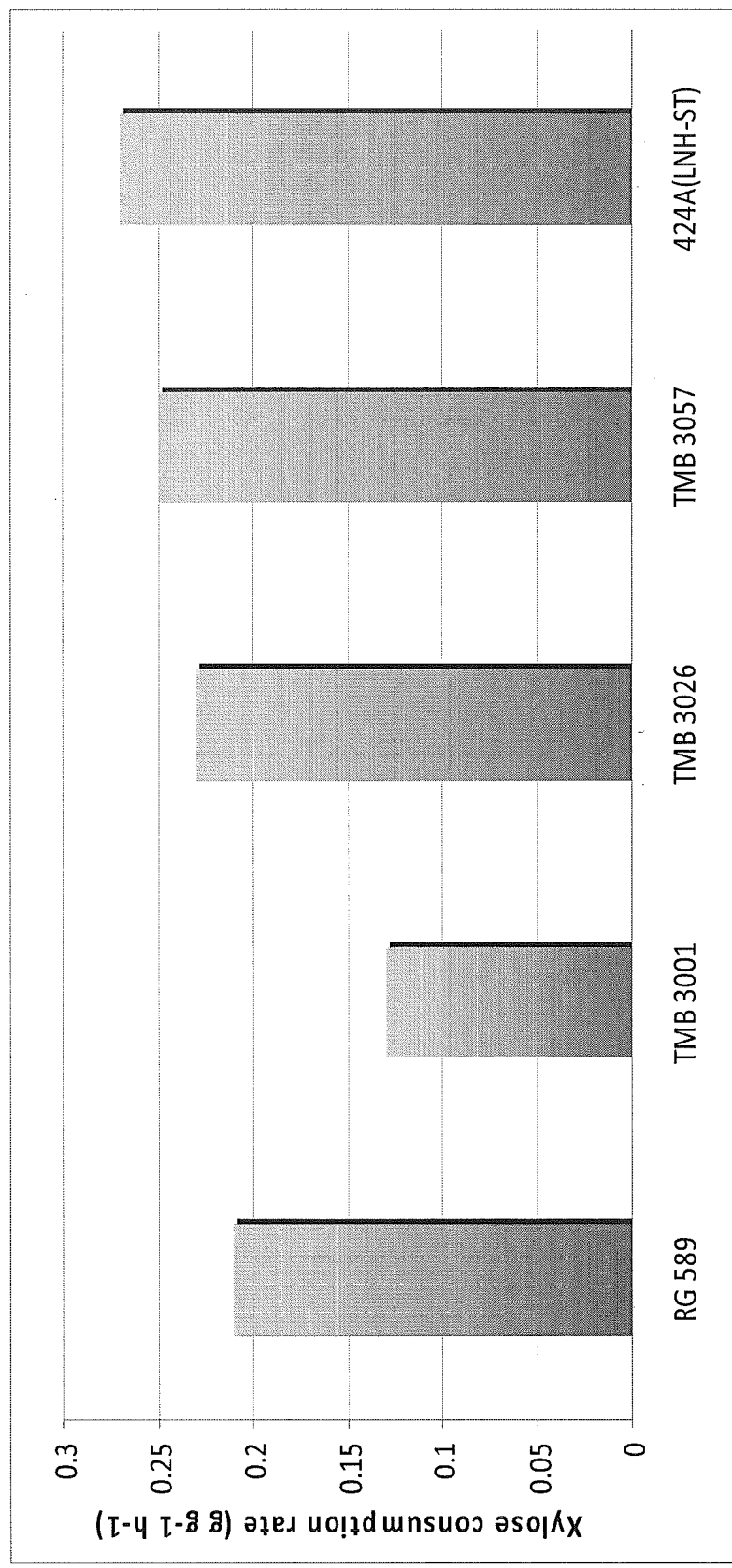
FIG. 1 shows the xylose consumption rates of the different strains mentioned in Example 2.

The invention utilizes cloning and transformation techniques in combination with mutation and strain taming techniques to obtain yeasts having high xylose consumption rate and ethanol yield. The cloning and transformation used in the invention are to transform xylose metabolism genes to yeasts to solve the problem that some yeast strains cannot utilize xylose to produce ethanol. The mutation and strain taming used in the invention are to increase xylose consumption rate and ethanol yield to solve the problem of low rate and yield. By combining the above-mentioned technical means, the invention unexpectedly obtain a mutant having high xylose consumption rate and ethanol yield.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

As used herein, the term "yield" refers to the amount of a product produced in relation to the amount of a starting material.

As used herein, the term "strain" refers to microorganisms of a particular species which have common characteristics.

Unless indicated to the contrary, the terms "strain" and "cell" are used interchangeably herein. As one skilled in the art would recognize, microorganism strains are composed of individual yeast cells. Further, individual microorganism cells have specific characteristics which identifies them as being members of their particular strain.

As used herein, the term "parent strain" refers to a strain of a microorganism subjected to mutagenesis to generate a microorganism of the invention. Thus, use of the phrase "parent strain" does not necessarily equate with the phrase "wild-type" or provide information about the history of the referred to strain.

As used herein, the term "mutation" refers to an insertion, deletion or substitution in a nucleic acid molecule.

As used herein, the term "mutagenesis" refers to a process whereby one or more mutations are generated in an organism's genetic material (e.g., DNA). With "random" mutagenesis, the exact site of mutation is not predictable, occurring anywhere in the chromosome of the microorganism.

As used herein, the phrase "cycle of mutagenesis" in general refers to the treatment of cells with a mutagen, or combination of mutagens, followed by culture of those cells to allow surviving cells to reproduce. In many instances, the mutagenized cells will be screened to identify those with particular characteristics after each cycle of mutagenesis. Further, as part of a cycle of mutagenesis, cells treated with a mutagen may be exposed to a selective agent or medium immediately after mutagenesis or while still exposed to the mutagen.

As used herein, the term "suitable fermentation condition" generally refers to fermentation media and conditions adjustable with, pH, temperature, levels of aeration, etc., preferably optimum conditions that allow microorganisms to produce carbon-based products of interest. To determine if culture conditions permit product production, the microorganism can be cultured for about 24 hours to one week after inoculation and a sample can be obtained and analyzed. The cells in the sample or the medium in which the cells are grown are tested for the presence of the desired product.

In one aspect, the invention provides an isolated yeast strain which has xylose consumption rate higher than 1.1 g xylose/gram biomass/hour and comprises one or more xylose metabolism gene obtained from strain *Saccharomyces cerevisiae* FENC-000 with DSMZ Deposit No. 25508. In a preferred embodiment, the isolated yeast strain is an isolated strain of *Saccharomyces cerevisiae* FENC-000 with deposit number of DSMZ No. 25508.

In one embodiment, the yeast strains of the invention exhibit high xylose consumption rate; preferably, higher than 1.1 g xylose/g biomass/hour. More preferably, the xylose consumption rate is higher than 1.5 g xylose/g biomass/hour.

According to the invention, the yeast strains of the invention include, but not limited to, *Saccharomyces* strains, *Kluyveromyces* strains, *Pichia* strains and *Candida* strains. More preferably, the yeast strains of the invention include, but not limited to, *Saccharomyces cerevisiae* strains, *Saccharomyces carlsbergensis* strains, *Saccharomyces bulderi* strains, *Saccharomyces barnetti* strains, *Saccharomyces exiguus* strains, *Saccharomyces uvarum* strains, *Saccharomyces diastaticus* strains, *Saccharomyces carlsbergensis* strains, *Kluyveromyces lactis* strains, *Kluyveromyces marxianus* strains, *Kluyveromyces fungus* strains, *Pichia stipitis* strains, *Candida stellata* strains and *Candida shehatae* strains. Most preferably, the invention provides an isolated strain of *Saccharomyces cerevisiae* FENC-000 with deposit number of DSMZ No. 25508.

Xylose is a five-carbon aldose (pentose, monosaccharide) that can be catabolized or metabolized into useful products by a variety of organisms. According to the invention, the xylose metabolism genes include one or more gene selected from the group consisting of xylose reductase gene, xylitol dehydrogenase gene, xylulokinase gene and xylose isomerase.

According to the invention, the yeast strain of the invention is produced on the basis genetic cloning, transformation, mutagenesis, cycle of mutagenesis and strain taming. In one embodiment, the yeast strain of the invention is produced by cloning xylose metabolism genes and transforming these genes into a parent strain to obtain a transformed strain. Plasmids carrying an antibiotic resistance marker gene, such as kan (which encodes for kanomycin resistance) may be constructed and used as a vehicle to deliver the desired xylose metabolism genes into the chromosome. The xylose metabolism genes may be isolated by digestion with a suitable restriction enzyme and purified, and then introduced, through transformation or electroporation, into a host cell. In one embodiment of the invention, *S. cerevisiae* BCRC 22743 is the host for transformation.

Subsequently, the transformed strain is mutated with a mutagen. The invention is not limited to cells which exhibit high xylose consumption rate and ethanol yield. In other words, the invention includes cells which are characterized by the ability to highly consume xylose upon growth in culture for specified periods of time. In specific embodiments, the strains of the invention are produced by subjecting yeast cells containing relevant xylose metabolism genes on the chromosome under the control of a non-native promoter to one, two, three, four, five, or more cycles of mutagenesis followed by screening to identify cells demonstrating high xylose consumption rate.

A considerable number of methods for performing metagenesis are known in the art and can be used to generate bacterial strains of the invention. In general, these methods involve the use of chemical agents or radiation for inducing mutations. Examples of classes of chemical compound used in mutagenic procedures include, but not limited to, ethyl methanesulfonate (EMS), N-methyl-N-nitrosourea N-nitroso-N,N-diethylamine (NDEA) and N-ethyl-N'-nitro-N-nitrosoguanidine (ENNG), hydroxylamine, bisulfites and nitrofurans (e.g., 7-methoxy-2-nitronaphtho [2,1-p]furan), which have been known in the art to induce mutations in nucleic acid molecules. One skilled in the art would understand how to adjust the concentrations of the mutagenic agent and/or the particular conditions to achieve a desired mutation rate.

After cells have been subjected to mutagenesis, they can be screened to determine whether they have particular characteristics as described in the invention. Example of such characteristics include high xylose consumption rate and ethanol yield. Strains of the invention may be generated by using multiple cycles of mutagenesis and screening. After each mutagenic treatment, the mutagenized cells can be screened for increased xylose consumption rate.

In another aspect, the invention provides a process for producing ethanol, comprising the steps of: (a) fermenting medium containing a source of xylose or glucose with an isolated yeast strain according to the invention under a suitable fermentation condition; and (b) recovering the ethanol from said medium.

According to the invention, the isolated yeast strains of the invention are used for the fermentation of carbon source comprising a source of xylose or glucose. The source of xylose or glucose may be xylose or glucose as such or may be any carbohydrate oligo- or polymer comprising xylose or glucose units, such as e.g., lignocellulose, xylan, cellulose, starch and the like. For release of xylose or glucose units from such carbohydrates, appropriate carbohydrases (such as xylanases, glucanases, amylases and the like) may be added to the fermentation medium or may be produced by the transformed host cell. In the latter case the transformed host cell may be genetically engineered to produce and excrete such carbohydrases. In a preferred process the transformed host cell ferments both the xylose and glucose. In addition to a source of xylose (and glucose) as carbon source, the fermentation medium will further comprise the appropriate ingredient required for growth of the transformed host cell. Compositions of fermentation media for growth of microorganisms such as yeasts are well known in the art.

The fermentation process is a process for the production of a fermentation product such as ethanol, lactic acid, acetic acid, succinic acid, acrylic acid, citric acid, 3-hydroxy-propionie acid, amino acids, 1,3-propane-diol, ethylene, glycerol, beta-lactam antibiotics such as Penicillin G or Penicillin V and fermentative derivatives thereof and cephalosporins. The fermentation process may be an aerobic or an anaerobic fermentation process. An anaerobic fermentation process is herein defined as a fermentation process run in the absence of oxygen or in which substantially no oxygen is consumed, e.g., less than 5 mmol/L/h, and wherein organic molecules serve as both electron donor and electron acceptors. In the absence of oxygen, NADH produced in glycolysis and biomass formation, cannot be oxidized by oxidative phosphorylation. To solve this problem many microorganisms use pyruvate or one of its derivatives as an electron and hydrogen acceptor thereby regenerating NAD+. Thus, in a preferred anaerobic fermentation process pyruvate is used as an electron (and hydrogen acceptor) and is reduced to fermentation products such as ethanol, lactic acid, 1,3-propanediol, ethylene, acetic acid or succinic acid.

The fermentation process is preferably run at a temperature that is optimal for the transformed host cell. Thus, for most yeasts, the fermentation process is performed at a temperature which is less than 38° C. For yeast or filamentous fungal host cells, the fermentation process is preferably performed at a temperature which is lower than 37, 36, 35, 34, 33, 32, 31, 30, 29 or 28° C. and at a temperature which is higher than 20, 21, 22, 23, 24 or 25° C.

According to the invention, in the process the volumetric ethanol productivity is preferably at least 0.6 g ethanol per liter per hour; preferably, at least 0.7, 0.8, 0.9, 1.0, 1.1, 1.5, 2.0, 2.5, 3.0, 3.5, 4.0, 4.5 or, 5.0 g ethanol per liter per hour; more preferably, about 0.6 to about 2.5, or about 1.0 to about 3.0 g ethanol per liter per hour. The ethanol yield on xylose and/or glucose in the process preferably is at least 50, 60, 70, 80, 90, 95 or 98%.

The isolated yeast strain has unexpected xylose consummation rate and high ethanol yield, so the yeast strain is advantageous in production of ethanol through a fermentation process.

EXAMPLE

Example 1

Cloning of Xylose Metabolism Genes and Construction of Recombinant Plasmid

Thirty wild type strains obtained from the Food Industry Research and Development Institute (FIRDI) were cultured and selected using SX medium containing 10% ethanol and one strain having high tolerance to high level ethanol, *S. cerevisiae* BCRC 22743, was selected. The following genes were cloned using polymerase chain reaction (PCR) under the following conditions:
  1.pGK Promoter
  Length: 643 bp
  Type: DNA
  Original strain: *Saccharomyces cerevisiae*
  Gene annotation: pGK promoter

```
Primer forward:
                                    (SEQ ID NO: 1)
GACTACGCATGCGGCGCGAATCCTTTATTTTGGCTTC Primer reverse:
                                    (SEQ ID NO: 2)
TGAATTACTGAACACAACATTGTTTTATATTTGTTGTAAAAAGTAG
```

2. Xylose Reductase
Length: 957 bp
Type: DNA
Original strain: *pichia stipitis*
Gene annotation: Xylose reductase

```
Primer forward:
                                    (SEQ ID NO: 3)
AAAACAATGCCTTCTATTAAGTTGAACTCT Primer reverse:
                                    (SEQ ID NO: 4)
CAATTCAATTCAATTTAGACGAAGATAGGAATCTTGTC
```

3. Xylitol Dehydrogenase
Length: 1,092 bp
Type: DNA
Original strain: *pichia stipitis*
Gene annotation: Xylitol dehydrogenase

```
Primer forward:
                                    (SEQ ID NO: 5)
GACTACGCGGCCGCGGCGCGAATCCTTTATTTTGGCTTC Primer reverse:
                                    (SEQ ID NO: 6)
AAGGAAGGGTTAGCAGTCATTGTTTTATATTTGTTGTAAAAAGTAG
```

4. Xylulokinase
Length: 1,803 bp
Type: DNA
Original strain: *Saccharomyces cerevisiae*
Gene annotation: Xylulokinase

```
Primer forward:
                                    (SEQ ID NO: 7)
AAAACAATGTTGTGTTCAGTAATTCAGAG Primer reverse:
                                    (SEQ ID NO: 8)
CAATTCAATTCAATTTAGATGAGAGTCTTTTCCAGTTCG
```

5. pGK Terminter
Length: 433 bp
Type: DNA
Original strain: *Saccharomyces cerevisiae*
Gene annotation: pGK terminter

```
Primer forward:
                                    (SEQ ID NO: 9)
GACTCTCATCTAAATTGAATTGAATTGAAATCGATAG Primer reverse:
                                    (SEQ ID NO: 10)
TAGAGTCCCGGGAGTCTGCTCGAGGAGATGCGGCCGCGACTTTTTTTGTT
GCAAGTGGGAT
```

The cloned genes were introduced into pAUR101 plasmid to construct a recombinant vector using genetic engineering techniques known in the art [Li L, Shugiu C, Anja J V B, Eric B K. Rad51p and Rad54p, but not Rap52p, elevate gene repair in *Saccharomyces cerevisiae* directed by modified single-stranded oligonucleotide vectors, 2002, *Nucleic Acids Research* 30:2742-2750]. *S. cerevisiae* BCRC 22743 was treated to form a competence cell and transformed with the recombinant vector so that xylose reductase, xylitol dehydrogenase and xylulokinase genes can be introduced into genomic DNA of *S. cerevisiae* BCRC 22743. The resulting transformants were selected to obtain the transformed strains capable of using xylose and producing ethanol.

Example 2

Xylose Metabolism and Ethanol Production of the Selected Transformant

Five transformed strains capable of using xylose and producing ethanol were selected from over 1,000 *S. cerevisiae* transformants according to the procedures stated in Example 1 and were named as *S. cerevisiae* RG 352, *S. cerevisiae* RG 758, *S. cerevisiae* RG 316, *S. cerevisiae* RG 527 and *S. cerevisiae* RG 589. Among the selected strains, *S. cerevisiae* RG 589 is able to produce highest ethanol concentration (16 g/L) in 5% SX medium and achieve 0.21 g xylose/g biomass/hour of xylose consumption rate. However, the above-mentioned results are better than those of strain TMB 3001 but do not have significantly differences from those of the strains TMB 3026, TMB 3057 and 422A (LNH-ST). The comparative xylose consumption rates are shown in FIG. 1.

Example 3

Preparation of Mutants of *S. cerevisiae* RG 589

Figure 2:
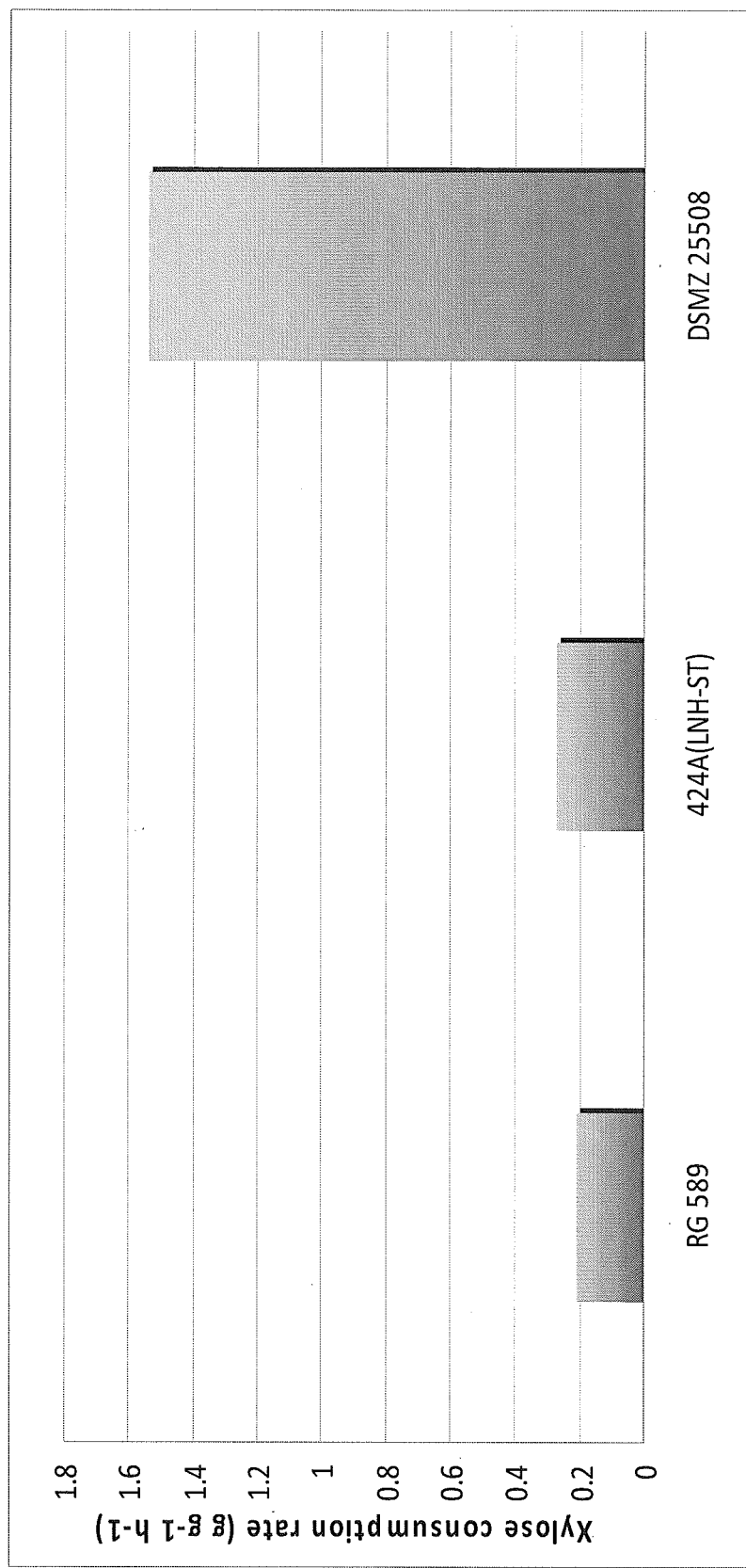
FIG. 2 shows the xylose consumption rates of *S. cerevisiae* mutants mentioned in Example 3.

*S. cerevisiae* RG 589 cells were treated with ethyl methanesulfonate (EMS) solution for 20 minutes to obtain mutants. The resulting solution was centrifuged and the supernatant was removed. The residual cell pellet was washed with 0.1 M phosphate buffer (pH 6) twice. After appropriate dilution, the cells were inoculated in 5% SX medium (Yeast Nitrogen Base 4.7 g/L and, Xylose 50 g/L) and cultured at 30° C. with 200 rpm shaking. If a mutant cultured at a concentration of 50 g/L xylose can utilize xylose for maintainence, growth, metabolism and production of ethanol, it has better ability in using xylose. After culturing the mutants at the concentration of 50 g/L xylose for three days, the mutants were taken out and then performed the above-mentioned mutation and culture process twenty times. The resulting mutants were plated at SX medium plate for mutant selection. After two days, the mutant growing fast was selected and named as *S. cerevisiae* FENC-000 that was deposited with Deutsche Sammlung von Mikroorganismen and Zellkulturen (DSMZ) under deposit number25508. After cultured the selected mutant with SX 5% medium at 30° C. with 200 rpm shaking for 24 hours, the xylose consumption rate reaches 1.54 g xylose/g biomass/hour, which is 5 to 7.14-fold higher than RG is 589 and 422A (LNH-ST). The results are shown in FIG. 2.

Example 4

Production of Ethanol with *S. cerevisiae* FENC-000 and Comparative Yields

*S. cerevisiae* FENC-000 (i.e., DSMZ 25508) mentioned in Example 3 and *S. cerevisiae* RG 589 mentioned in Example 2 were cultured with SX medium mixed with one or two carbon sources at 30° C. with 200 rpm shaking. The ethanol yields are shown in the below table.

| Strain | Carbon source | Ethanol yield (g g−1) | Ethanol productivity (g l−1 h−1) |
|---|---|---|---|
| RG 589 | 90 g/L glucose and 30 g/L xylose | 0.33 | 0.83 |
| DSMZ 25508 | 90 g/L glucose and 30 g/L xylose | 0.46 | 1.152 |
| RG 589 | 50 g/L xylose | 0.309 | 0.482 |
| DSMZ 25508 | 50 g/L xylose | 0.402 | 0.629 |
| DSMZ 25508 | 110 g/L glucose and 50 g/L xylose | 0.363 | 1.95 |
| Pichia stipitis CBS 7126 | 50 g/L xylose | 0.43 | 0.9 |
| Pichia stipitis FPL-Shi3I | 80 g/L xylose | 0.31 | 0.15 |
| S. cerevisiae 1400 (pLNH32) | 90 g/L glucose and 40 g/L xylose | 0.46 | 1.15 |
| S. cerevisiae TMB 3001 | 50 g/L glucose and 50 g/L xylose | 0.23 | 0.12 |
| S. cerevisiae TMB 3001 | 15 g/L glucose and 5 g/L xylose | 0.3 | 0.41 |

*S. cerevisiae* FENC-000 exhibits 1.3-fold higher ethanol yield than that of *S. cerevisiae* RG 589 when using 50 g/L xylose. For using two sugars as carbon source, *S. cerevisiae* FENC-000 exhibits around 1.394- and 2-fold higher ethanol yield than that of RG 589 and TMB 3001, respectively.

What is claimed is:

1. An isolated strain of *Saccharomyces cerevisiae* FENC-000 with deposit number of DSMZ No. 25508.

2. The isolated strain of claim 1, which has a xylose metabolism gene selected from the group consisting of xylose reductase gene, xylitol dehydrogenase gene, xylulokinase gene and xylose isomerase.

3. The isolated strain of claim 1, which is obtained by cloning one or more of more xylose metabolism gene, transforming the gene into a host yeast strain, mutating the resulting strain with a mutagen and selecting the yeast strain having xylose consumption rate higher than 1.1 g xylose/gram biomass/hour.

4. The isolated strain of claim 1, which can produce ethanol and at least one of lactic acid, acetic acid, succinic acid, acrylic acid, citric acid, 3-hydroxy-propionie acid, amino acids, 1,3-propane-diol, ethylene, glycerol, beta-lactam antibiotics and cephalosporins.

* * * * *

SEQUENCE LISTING

```
<160> NUMBER OF SEQ ID NOS: 10

<210> SEQ ID NO 1
<211> LENGTH: 37
<212> TYPE: DNA
<213> ORGANISM: Artificial Sequence
<220> FEATURE:
<223> OTHER INFORMATION: Primer

<400> SEQUENCE: 1
gactacgcat gcggcgcgaa tcctttattt tggcttc                              37

<210> SEQ ID NO 2
<211> LENGTH: 46
<212> TYPE: DNA
<213> ORGANISM: Artificial Sequence
<220> FEATURE:
<223> OTHER INFORMATION: Primer

<400> SEQUENCE: 2
tgaattactg aacacaacat tgttttatat ttgttgtaaa aagtag                    46

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
aaaacaatgc cttctattaa gttgaactct                                      30

<210> SEQ ID NO 4
<211> LENGTH: 38
<212> TYPE: DNA
<213> ORGANISM: Artificial Sequence
<220> FEATURE:
<223> OTHER INFORMATION: Primer

<400> SEQUENCE: 4
caattcaatt caatttagac gaagatagga atcttgtc                             38

<210> SEQ ID NO 5
<211> LENGTH: 39
<212> TYPE: DNA
<213> ORGANISM: Artificial Sequence
<220> FEATURE:
```

<223> OTHER INFORMATION: Primer

<400> SEQUENCE: 5
gactacgcgg ccgcggcgcg aatcctttat tttggcttc                          39

<210> SEQ ID NO 6
<211> LENGTH: 46
<212> TYPE: DNA
<213> ORGANISM: Artificial Sequence
<220> FEATURE:
<223> OTHER INFORMATION: Primer

<400> SEQUENCE: 6
aaggaagggt tagcagtcat tgttttatat ttgttgtaaa aagtag                  46

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
aaaacaatgt tgtgttcagt aattcagag                                     29

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
caattcaatt caatttagat gagagtcttt tccagttcg                          39

<210> SEQ ID NO 9
<211> LENGTH: 37
<212> TYPE: DNA
<213> ORGANISM: Artificial Sequence
<220> FEATURE:
<223> OTHER INFORMATION: Primer

<400> SEQUENCE: 9
gactctcatc taaattgaat tgaattgaaa tcgatag                            37

<210> SEQ ID NO 10
<211> LENGTH: 61
<212> TYPE: DNA
<213> ORGANISM: Artificial Sequence
<220> FEATURE:
<223> OTHER INFORMATION: Primer

<400> SEQUENCE: 10
tagagtcccg ggagtctgct cgaggagatg cggccgcgac tttttttgtt gcaagtggga   60
t                                                                   61